United States Patent
Witkin

(10) Patent No.: US 6,828,113 B2
(45) Date of Patent: Dec. 7, 2004

(54) IGM ANTIBODIES TO THE 70 KDA HEAT SHOCK PROTEIN AS A MARKER FOR CYTOMEGALOVIRUS INFECTION

(75) Inventor: Steven S. Witkin, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 39 days.

(21) Appl. No.: 10/394,491

(22) Filed: Mar. 21, 2003

(65) Prior Publication Data

US 2003/0180721 A1 Sep. 25, 2003

Related U.S. Application Data

(60) Provisional application No. 60/366,428, filed on Mar. 21, 2002.

(51) Int. Cl.$^7$ .............................. G01N 33/53
(52) U.S. Cl. .................. 435/7.1; 435/7.94; 424/193.1; 424/198.1; 424/806
(58) Field of Search ................. 435/7.1, 7.94; 424/193.1, 198.1, 806

(56) References Cited

PUBLICATIONS

A. Figueredo, et al., "Increased Serum Levels of IgA Antibodies to hsp70 Protein in Patients with Diabetes Mellitus: Their Relationship with Vascular Complications", *Clinical Immunology and Immunopathology*, vol. 79, No. 3, pp. 252–255 (1996).

Manxin Zhang, et al., "Antibodies Specific for Heat Shock Proteins in Human and Murine Malaria", *Microbes and Infection*, vol. 3, pp. 363–367 (2001).

G. Hayem, et al., "Anti–Heat Shock Protein 70 kDa and 90 kDa Antibodies in Serum of Patients with Rheumatoid Arthritis", *Ann. Rheum. Dis.*, vol. 58, pp. 291–296 (1999).

Gisela Enders, et al., "Prenatal Diagnosis of Congenital Cytomegalovirus Infection in 189 Pregnancies with Known Outcome", *Prenatal Diagnosis*, vol. 21, pp. 362–377 (2001).

Ahmad–Zalmai Azam, et al., "Prenatal Diagnosis of Congenital Cytomegalovirus Infection", *Obstet Gynecol*, vol. 97, pp. 443–448 (2001).

Eriko Ohgitani, et al., "Biphasic Translocation of a 70 kDa Heat Shock Protein in Human Cytomegalovirus–Infected Cells", *Journal of General Virology*, vol. 80, pp. 63–68 (1999).

Gregory T. Maine, et al., "New Developments in the Diagnosis of Maternal and Congenital CMV Infection", *Expert Rev. Mol. Diagn.*, vol. 1, No. 1, pp. 19–29 (2001).

T. Lazzarotto, et al., "New Advances in the Diagnosis of Congenital Cytomegalovirus Infection", *Intervirology*, vol. 42, pp. 390–397 (1999).

Oral Disclosure, Apr. 28, 2001, Conference—Int'l Infect. Disease Society for Ob/Gyn.

*Primary Examiner*—Ali R. Salimi

(57) ABSTRACT

The present invention provides a method for detecting the presence of cytomegalovirus (CMV) in a fetal sample by determining the presence of anti-hsp70 antibodies present in the fetal sample. The invention further provides a method for monitoring CMV infection in a human fetus. In another embodiment, the invention provides a method for detecting CMV in a cord blood sample of a neonate.

23 Claims, No Drawings

IGM ANTIBODIES TO THE 70 KDA HEAT SHOCK PROTEIN AS A MARKER FOR CYTOMEGALOVIRUS INFECTION

This application asserts the priority of U.S. provisional application Ser. No. 60/366,428 filed Mar. 21, 2002, the specification of which is hereby incorporated by reference in its entirety.

BACKGROUND OF THE INVENTION

The heat shock proteins (hsps) are synthesized by a host cell in response to physical, chemical or biological stresses. A typical example of a biological stress includes infection of a host cell with a virus.

One member of hsps is the family of proteins known as hsp70. The function of hsp70 is to assist in thermotolerance, prevention of misfolding of nascent polypeptides, transmembrane protein transport and nuclear protein transport (Welch, 1993).

A virus that induces the expression of hsp70 in humans is the human cytomegalovirus (CMV). CMV is a member of the herpesvirus family.

Expression of hsp70 may be induced by several CMV proteins that activate the hsp70 promoter. These CMV proteins include the CMV immediate-early proteins 1 (IE1) and 2 (IE2), and the US3 and UL37 gene products (Hagemeir et al., 1992). The hsp70 protein has no known function in the virus replication cycle, but theoretically may assist in assembly of the CMV virion.

CMV is the most common viral intrauterine infectious agent, affecting 0.5–2.5% of all live births (Hagay et al., 1996). The infectious virus reaches the uterus via the bloodstream. The virus then traverses the placenta and infects the developing fetus. Such fetal CMV infections are called congenital infections.

Transmission of the virus to the fetus may occur as a result of either a primary maternal CMV infection or a recurrent maternal CMV infection. A primary maternal CMV infection is the initial infection of the mother with CMV. In contrast, a recurrent infection occurs as a result of reactivation of endogenous latent CMV or a reinfection with a new strain of CMV.

The transmission of CMV to a fetus may occur any time throughout a pregnancy. Primary maternal infection poses the major risk for congenital infection with a transmission rate of approximately 30–40%. The rate of transmission for a recurrent infection is about 0.15–1%.

Ten percent of congenitally infected infants develop congenital CMV syndrome (eg., death, encephalitis, neurological problems, etc.) while 90% are asymptomatic at birth (Hagay et al., 1996). Of the 10% of congenitally CMV infected infants, approximately 20% die and 72% develop major neurological problems.

Of the 90% of congenitally infected infants that are asymptomatic at birth, 5–7% will be afflicted by late sequelae. The late sequelae include mental retardation, deafness, and hearing defects. These symptoms usually appear during the first two years of life (Demmler 1994; Stagno et al., 1986).

Diagnosis of congenital CMV infection is typically made by detecting CMV in the amniotic fluid by culture or polymerase chain reaction (PCR). This method yields a sensitivity of about 70–100% (Hagay et al., 1996; Levy et al., 1996; Bodeus et al., 1999; Donner et al., 1993).

CMV infection in the first or second trimester of pregnancy typically results in an outcome for the fetus or the newborn that is less favorable than CMV infection in the third trimester (Stagno et al., 1986). Early detection, especially in the first trimester or early in the second trimester, would facilitate the option to terminate the pregnancy. Therefore, early detection of fetal CMV infection is important.

CMV infection is typically detected by assaying for CMV in amniotic fluid. However, in order to reliably detect CMV in amniotic fluid, the amniocentesis must be performed after 21 weeks of gestation (i.e., almost the end of the second trimester), and at least six weeks after seroconversion (Grangeot-Keros et al., 2001).

Another problem with detecting CMV by amniocentesis is that detection of CMV in amniotic fluid merely differentiates infected from uninfected fetuses. This method for detecting CMV does not reveal the extent of infection in the fetus.

Accordingly, detecting CMV in amniotic fluid does not accurately determine fetal outcome. An accurate determination of fetal outcome is important in order to provide appropriate counseling for parents.

Commercial ELISA kits that measure CMV-specific antibodies have also been used to detect congenital CMV infection (Azam et al., 2001). The antigen used for detection of CMV-specific antibodies in the ELISA is typically either a specific structural protein (e.g., pUL32, pUL83, pUL80a) or a specific nonstructural protein (e.g., pUL57, pUL44).

These commercial ELISA kits are used in assays in which blood is taken from a patient at a time that corresponds to a point in the life cycle of the virus. Various viral proteins are produced in different amounts during the life cycle of the virus. The variation in amounts of viral proteins produced by the virus results in differences in the amounts of antibodies, produced by the patient, to the viral proteins.

Since the commercial ELISA kits measure the amount of antibodies to a specific viral protein, the result of the assay depends on when blood is obtained and on which protein the commercial kit uses as an antigen. Therefore, the correlation of results obtained with different commercial kits that measure CMV-specific antibodies is poor (Lazzarotto et al., 1992). Contradictory results may be obtained if a serum sample is tested with two different kits. The sensitivity of these commercial ELISA is reported to be only 20–70% (Hogge et al., 1993; Hohlfeld et al., 1991).

Therefore, there is an immediate need for a reliable method for detecting congenital CMV infection and for determining the extent of the infection in a fetus. In addition, since about 10% of asymptomatic newborns will suffer late sequelae of a CMV infection, there is a need to assess CMV infection in a neonate at the time of birth.

SUMMARY OF THE INVENTION

The above needs have been satisfied by providing a method for detecting the presence of CMV in a fetal sample. The method comprises obtaining a fetal sample from a human fetus of an expectant mother infected with CMV, and determining the presence of anti-hsp70 antibodies in the fetal sample. The presence of anti-hsp70 antibodies indicates the presence of CMV in the fetal sample.

In another embodiment, the invention provides a method for monitoring CMV infection in a human fetus. The method comprises obtaining a first fetal sample from the fetus of an expectant mother infected with CMV, determining the amount of anti-hsp70 antibodies in the first fetal sample, obtaining a subsequent fetal sample, and determining the amount of anti-hsp70 antibodies in the subsequent fetal sample. A change in the first sample compared to the subsequent sample indicates a change in the infection. Such changes permit monitoring of CMV infection in the fetus.

In yet another embodiment, the invention provides a method for detecting the presence of CMV in a cord blood sample of a neonate. The method comprises obtaining the cord blood sample and determining the presence of anti-hsp70 antibodies in the sample. The presence of anti-hsp70 antibodies in the sample indicates the presence of CMV in the cord blood sample.

DETAILED DESCRIPTION OF THE INVENTION

The present invention is based on the discovery by the inventor that IgM antibodies to hsp70 are produced by a fetus as a result of congenital CMV infection, and that an assay for such IgM antibodies constitutes a reliable measure of CMV infection.

In one embodiment, the invention relates to a method for detecting the presence of CMV in a sample. The sample may be a fetal sample or a cord blood sample from a neonate.

A fetal sample refers to any fluid in the fetus or enclosed by the amniotic sac, including the umbilical cord, that may contain antibodies from a fetus. Examples of fetal samples include fetal sera, fetal blood, cord blood, and amniotic fluid. A human fetus is typically defined as existing from about the eighth week after conception to the moment of birth.

A cord blood sample from a neonate is obtained from the umbilical cord shortly after birth. A neonate is typically defined as existing from birth until about four weeks.

The first step in the method is obtaining a fetal sample or a cord blood sample from a neonate. The fetal sample may be collected by any method known in the art. For example, fetal sera can be derived from the blood of a developing fetus. Fetal blood (e.g., cord blood) may be obtained from the umbilical cord by cordocentesis as described in Daffos et al., 1985.

Alternatively, the fetal sample may be obtained from the amniotic fluid. Amniotic fluid may be obtained by any method known in the art, for example by amniocentesis (see for example, Marthin et al., 1997).

The fetal samples may be obtained at any time during fetal development. For example, the fetal sample may be obtained during the first trimester, second trimester, and/or third trimester.

A cord blood sample from a neonate may be obtained from the umbilical cord of the neonate by any method known in the art. Preferably, the cord blood sample is obtained within about 24 hours after birth, more preferably within about six hours, and most preferably within about two hours after birth of the neonate.

It is important to note that, in one embodiment, a fetal sample can be a cord blood sample, which is obtained from the umbilical cord of a fetus before birth. In another embodiment, a sample is a cord blood sample of a neonate, which is taken from the umbilical cord after birth.

The second step in the method of the above embodiment is determining the presence of anti-hsp70 antibodies in the sample. Determining the presence of anti-hsp70 antibodies may be accomplished by any method known in the art. Some examples include immunoassays such as, for example, an ELISA (Current Protocols in Immunology, Wiley Intersciences, New York, 1999) and a standard blot assay (Towbin et al., 1979 and Towbin et al., 1984). These assays are described in more detail below.

Determining the presence of anti-hsp70 antibodies may be qualitative. For example, the presence of anti-hsp70 antibodies may be indicated by means of an assay that leads to a detectable signal, such as a change in color or the emission of radioactivity, as compared to that of a control sample. Such a change indicates the presence of anti-hsp70 antibodies, thereby indicating the presence of CMV in the sample.

A control sample, depending on the particular embodiment, is typically a fetal sample from an uninfected fetus or a cord blood sample from an uninfected neonate. For example, if the method is used to detect the presence of CMV in a fetal sample, then the control sample is typically a fetal sample from an uninfected fetus. However, if the method is used to detect the presence of CMV in a cord blood sample of a neonate, the control sample is typically a cord blood sample from an uninfected neonate.

The above method for determining the presence of anti-hsp70 antibodies may further comprise determining the amount of anti-hsp70 antibodies in the sample relative to the amount of anti-hsp70 antibodies in a control sample. The quantitative assays for determining this amount may, for example, use known quantities (i.e., standards) of anti-hsp70 antibodies. These standards may be used to generate a standard curve that relates a concentration of anti-hsp70 antibodies to the quantity of a detectable signal. The detectable signal can be, for example, the quantity of light emitted or absorbed (e.g., optical density) or quantity of radioactivity emitted (e.g., radioactive counts per minute).

For example, a graph of known concentrations of anti-hsp70 antibodies versus optical density or radioactive counts may be used to calculate the amount (e.g., concentration) of anti-hsp70 antibodies in the sample. The amount of anti-hsp70 antibodies detected in a sample using a quantitative assay is typically compared to the amount of anti-hsp70 antibodies in a control sample (i.e., background amount).

It is not, however, necessary to generate a standard curve or to calculate the amount of anti-hsp70 antibodies in a sample. Alternatively, the quantity of the detectable signal (e.g., light absorbed or emitted, or radioactivity emitted) from a sample to that of a control sample (i.e., background signal) may be used as a measure of the amount of anti-hsp70 antibodies in the sample relative to the control sample. The quantity of detectable signal is indicative of the amount of anti-hsp70 antibodies present in the sample since an increase in optical density or radioactive counts correlate with an increase in the concentration of anti-hsp-70 antibodies. Accordingly, the quantity of detectable signal may be used as a measure of the amount of anti-hsp70 antibodies.

It is not necessary to determine the background amount or the quantity of background signal each time an assay is conducted. It is well known in the art to compare the amount of ant-hsp70 antibodies or the quantity of detectable signal obtained as a measure of the amount of anti-hsp70 antibodies in the test sample to that of a previously determined background amount or background signal.

An amount of anti-hsp70 antibodies significantly elevated over that of the control indicates the presence of CMV in the sample. (It is understood that, as used herein, the amount of anti-hsp70 antibodies may be indicated by the quantity of the detectable signal.)

If the amount of anti-hsp70 antibodies in the control is a mean value, and the standard deviation of the mean value is known, or can be calculated, an amount is considered to be significantly greater if the amount is at least two standard deviations greater than the mean value of the control. If the standard deviation is not known, and cannot be calculated, an amount is significantly greater if the amount is at least about 10%, preferably at least about 25%, more preferably at least about 50%, even more preferably at least about 75%, and most preferably at least about 100% greater than that of the control. If no anti-hsp70 antibodies can be detected in the control, an amount of anti-hsp70 antibodies is significant if it can be detected in the sample.

The amount of anti-hsp70 antibodies present in the sample may be used to indicate the outcome of a fetus or neonate infected with CMV. For example, the amount of anti-hsp70 antibodies present may be an amount that is sufficient to cause congenital CMV syndrome. The amount sufficient to cause congenital CMV syndrome is typically at least about 100%, more typically at least about 150%, and most typically at least about 200% greater than the control. Some consequences of congenital CMV syndromes include, for example, deafness, neurological disorders, encephalitis and, in extreme cases, death.

In contrast, the amount may be an amount that is sufficient to cause the fetus to be asymptomatic at birth. For example, the amount that is asymptomatic is typically at most about 10%, more typically at most about 50%, and most typically at most about 100% greater than the control. Such an amount of anti-hsp70 antibodies may, however, be sufficient to cause late sequelae. Some examples of late sequelae include mental retardation, deafness, and hearing defects.

The amount of anti-hsp70 antibody may not be statistically different from that of the control. A non-statistically different amount would typically indicate that the fetus or neonate is not infected with CMV or that the fetus or neonate had not yet seroconverted. As used herein, seroconverted means that a fetus or neonate has not yet developed antibodies to hsp70. Preferably, the fetus would continue to be monitored for CMV infection. In addition, infected fetuses may also be monitored for CMV infection to determine the effect of administration of anti-viral drugs on the CMV infection.

In yet another embodiment, the invention relates to a method for monitoring CMV infection in a human fetus. The first step in the method is obtaining a first fetal sample.

The first fetal sample may be obtained at any time throughout fetal development. Preferably, the first sample is obtained during the first trimester. For example, the first sample may be taken at approximately ten weeks by amniocentesis or at approximately twenty-two weeks by cordocentesis.

The second step in the monitoring method is determining the amount of anti-hsp70 antibodies in the first fetal sample. The amount of anti-hsp70 antibodies may be determined by the methods described above.

The third step in the monitoring method is obtaining a subsequent fetal sample. One or more subsequent samples may be collected at various intervals throughout fetal development. The intervals can be determined by those in the art. For example, the second sample can be obtained about one, two, three, or four or more weeks after obtaining the first fetal sample. The amount of anti-hsp70 antibodies in the additional subsequent fetal samples can be determined as described above.

A change in the amount of anti-hsp70 antibodies in the first sample compared to the subsequent sample indicates a change in the CMV infection. The change may be, for example, an increase in the amount of anti-hsp70 antibodies, a decrease in the amount of anti-hsp70 antibodies, or a change in the infection status. An increase in the amount of anti-hsp70 antibodies detected indicates the progression of CMV infection. A decrease in the amount of anti-hsp70 antibodies detected may indicate the regression of the infection. The regression of CMV infection may occur, for example, as a result of anti-viral treatments. A change in the infection status of the fetus from uninfected to infected indicates seroconversion of the fetus.

The CMV that is useful in the methods of the present invention may be any strain of CMV. Preferably, the CMV is a clinical strain of CMV. Some examples of CMV strains include, but are not limited to, AD-169, UL37, and Towne. Preferably, the CMV is a human CMV.

The expectant mother may come into contact with CMV in several ways. Typically, infection occurs as a result of contacting body fluids from another individual infected with CMV.

The expectant mother may be infected with CMV at any time. For example, the expectant mother may be infected any time prior to conception, during conception, or at any time throughout the pregnancy.

Transmission of CMV from the mother to the human fetus may occur as a result of a maternal primary infection or a maternal recurrent infection. A maternal primary CMV infection is the first, initial infection of the expectant mother with the virus. A maternal recurrent CMV infection is an infection that typically occurs as a result of the reactivation of endogenous latent CMV or a re-infection with a new strain of CMV. An expectant mother with either a primary or recurrent CMV infection is said to be infected with CMV.

The CMV may be transmitted from the mother to the fetus at any time during the pregnancy. Transmission of the virus from the mother to the fetus may occur in several ways. Typically the infectious virus reaches the uterus through the bloodstream and crosses the placenta to infect the developing fetus.

Anti-hsp70 antibodies that can be assayed in accordance with the methods of the invention are anti-hsp70 antibodies produced by the fetus in response to CMV. The anti-hsp70 antibodies may, for example, be an antibody to hsp70 or an antibody to hsp70 complexed to another molecule. The other molecule may, for example, be a human molecule, typically a human protein.

Alternatively, the other molecule may, for example, be a CMV viral molecule, typically a CMV viral protein. The CMV viral proteins may, for example, be structural or nonstructural proteins. Some examples of CMV viral proteins include, but are not limited to, pUL32, pUL83, pUL80a, pUL57, and pUL44.

The antibodies may be any class of antibody. In humans, for example, there exists five isotypes: immunoglobin (Ig) G, IgA, IgM, IgD, and IgE. Preferably, the antibodies are of the IgM isotype.

General Methods

Determining the presence of anti-hsp70 antibodies, amount of anti-hsp70 antibodies, or quantity of detectable signal can be preformed by any method known in the art. Some general methods and techniques are described below. More specific methods and techniques are found in the specific examples below.

As stated above, examples of methods and techniques include an ELISA assay and a standard blot assay. These assays are normally based on incubating a sample, suspected of containing the antibody, with a protein and detecting the presence of a complex between the antibody and the protein.

For example, the protein is preferably immobilized prior to detection and is referred to as a capture antigen. For the purposes of this invention, the capture antigen is typically hsp70. Immobilization may be accomplished by directly binding the capture antigen to a solid surface, such as a microtiter well. If anti-hsp70 antibodies are present in the sample, the antibodies will bind to the capture antigen.

A second antibody is added that binds specifically to the isotype of the anti-hsp70 antibodies in the sample. Preferably, the second antibody will recognize the human IgM antibody isotype. The second antibody may be labeled by methods known in the art. The secondary antibody may, for example, be radiolabeled or enzymatically labeled. Preferably, the labeled second antibody is enzymaticaly labeled to provide, for example, visual or photometric analysis. Examples of such enzymatic labels include, for example, horse radish peroxidase and alkaline phosphatase. Some examples of photometric instruments that may be used for analysis include, for example, a spectrophotometer and an ELISA plate reader.

In general, it is desirable to provide incubation conditions sufficient to cause binding of as much antibody present in the sample as possible. The specific concentrations of labeled second antibodies, the temperature and time of incubation, as well as other such assay conditions, can be varied, depending upon various factors including the concentration of anti-hsp70 antibodies in the sample, the nature of the sample and the like. Those skilled in the art will be able to determine operative and optimal assay conditions for each determination by employing routine experimentation.

EXAMPLES

Example 1

Materials and Methods

In Switzerland, routine screening of pregnant women exists in an attempt to prevent congenital CMV infection. Repetitive serum samples of all seronegative patients allows the clinician to detect and date seroconversion. To determine the relation between IgM antibodies to hsp70 and fetal CMV infection, fetal sera obtained by cordocentesis during 22–25 weeks of gestation from 53 mothers who developed a primary CMV infection during the first trimester of pregnancy between July 1990 to August 2000 were analyzed. As controls, 28 fetal sera obtained from mothers being screened for Rh incompatibility were also tested. Any woman presenting with another recent infection was excluded (i.e., hepatitis, herpes, parvovirus, syphillis, HIV, toxoplasmosis).

Informed consent was obtained from patients and human experimentation guidelines of the US Department of Health and Human Services were followed in the conduct of this research.

Serologic diagnosis of primary CMV infection was documented by seroconversion (i.e., appearance of de novo specific IgG and IgM antibodies in a patient who had been seronegative). The first serological test was performed at 8–12 weeks gestation. For seronegative women, a second and third test was performed at 16–18 and 20–22 weeks, respectively. If a positive test was reported a repeat test was performed in approximately two weeks. A CMV-specific IgG avidity test differentiated primary from non-primary infection (Grangeot-Keros et al., 1997; Lazzarotto et al., 1997). All patients with a CMV avidity index >65% were excluded. All maternal IgG and IgM tests were performed by the same laboratory. Prenatal diagnosis was evaluated by two methods in the 53 CMV-positive subjects, involving a combination of amniocentesis and chordocentesis under ultrasound guidance. Diagnosis of intrauterine CMV infection was obtained by isolation of the virus from amniotic fluid by culture or by identification of CMV DNA through PCR. When pregnancy termination was performed, viral cultures of fetal tissue were used to confirm the diagnosis and analyses for detection of CMV inclusions in fetal tissues were performed. For cases proceeding to birth, CMV isolation from the offspring's urine was systematically performed.

For all congenitally infected infants, complete follow-up information was obtained from pediatricians. For uninfected infants, information was collected from either the pediatrician or the parents in all cases but one that was lost to follow-up.

Sera were tested without knowledge of the final diagnosis for IgG and IgM antibodies to hsp70 as well as the 60 kDa heat shock protein (hsp60), used as an additional stress marker, by ELISA, using the purified recombinant proteins (StressGen, Victoria, BC) bound to wells of a microtiter plate (Witkin et al., 1998). Briefly, sera were diluted 1:10 in phosphate buffered saline-0.05% Tween 20 (PBS-Tween) and added to the wells containing 1 $\mu$g bound heat shock protein. After an incubation of 60 minutes in a 37° C. water bath, the wells were washed three times with PBS-Tween and incubated with 0.1 ml of a 1:200 dilution of alkaline phosphatase-conjugated goat antibody to human IgG or IgM. Following an additional 60 minutes at 37° C., the wells were again washed with PBS-Tween and the alkaline phosphatase substrate, p-nitrophenylphosphate in 10% diethanolamine buffer was added. The absorbance in each well was determined at 405 nm after 30 minutes using a microtiter plate reader (Titertek Inc, Huntsville, Ala.). A positive result was operationally defined as an optical density at least three standard deviations above the mean value obtained with the control sera. This value was 0.092 for anti-hsp70 IgM and 0.097 for anti-hsp70 IgG.

Data were compared between groups using the Mann-Whitney rank-sum test. p values of <0.05 were considered statistically significant.

Example 2

Detection of CMV by Amniotic Fluid Culture or PCR

The mean gestational age at the time of cordocentesis was 23 weeks (range 22 to 25 weeks) in all subjects and controls. As determined by amniotic fluid culture or PCR, 15 (28.3%) of the 53 fetuses were congenitally infected with CMV. An additional three fetuses were culture negative but testing performed after birth resulted in isolation of CMV from urine samples. Of the 18 infected fetuses, termination of pregnancy occurred in 8 cases. From each of these cases, tissue culture confirmed the diagnosis and CMV-inclusions were searched for in different tissues. From the 10 infected fetuses in which the pregnancy proceeded to delivery, one presented as a stillbirth at 38 weeks. At autopsy, tissue culture confirmed the CMV infection but no CMV-inclusions were identified in the different tissues. Amniotic fluid aspiration was the final diagnosis. Of the remaining 9 cases, two had congenital CMV syndromes, one had bilateral deafness at 6 months and one had unilateral hypoacousia and chorioretinitis at 3 months. The remaining five neonates had no detectable pathology.

Example 3

IgG and IgM Antibodies to hsp60 and hsp70 in Sera from CMV-infected and CMV-uninfected Fetuses Antibodies to hsp70 and hsp60 were determined in the 18 infected, the 35 uninfected, and the 28 control fetuses. Mean values and ranges are presented in Table 1.

The mean values for IgG anti-hsp70 antibodies were higher in fetuses of infected mothers than in controls (0.23 for fetuses from infected mothers and 0.07 for control fetuses; p<0.0001), regardless of whether or not the fetus was infected. In contrast, anti-hsp70 IgM was elevated only in CMV-infected fetuses and not in uninfected or control fetuses (0.17 for infected fetuses and 0.06 for uninfected and control fetuses; p<0.0001).

Results of anti-hsp60 IgG and IgM testing showed no statistically significant differences between sera of infected, uninfected or control fetuses, respectively (see Table 1).

Of the 53 mothers positive for CMV infection, 52 (98.1%) were positive for IgG anti-hsp70. Seventeen of the 18 CMV-infected fetuses (94.4%) were IgM anti-hsp70 positive. In marked contrast, only 3 of the 35 uninfected fetuses (8.6%) and none of the 28 controls were antibody positive (p<0.0001): Thus, as a screening test for CMV fetal infection, IgM anti-hsp70 had a sensitivity of 94%, a specificity of 91%, a positive predictive value of 85% and a negative predictive value of 97%.

TABLE 2

Relation between IgM anti-hsp70 optical density (O.D.) and fetal outcome in CMV-infected fetuses.

| O.D. | Birth | Termination | Outcome or pathology finding |
|---|---|---|---|
| 0.351 | | 1 | CMV inclusions in tissues |
| 0.294 | | 1 | CMV inclusions in tissues |
| 0.242 | | 1 | CMV inclusions in tissues |
| 0.230 | 1 | | Bilateral deafness |
| 0.212–0.228 | | 2 | CMV inclusions in tissues |
| 0.191 | 1 | | Unilateral hypoacousia, retinitis |
| 0.130–0.140 | 1 | | Stillbirth, no CMV inclusions |
| 0.130–0.140 | | 3 | one CMV inclusion in lung of one fetus, others without CMV inclusions |
| 0.072–0.124 | 7 | 0 | All normal |

References

Azam A Z, Vial Y, Fawer C L, Zufferey J, Hohlfeld P. Prenatal diagnosis of congenital cytomegalovirus infection. *Obst. Gynec.* (2001) 97:443–448.

TABLE 1

IgG and IgM antibodies to hsp60 and hsp70 in sera from CMV-infected and CMV-uninfected fetuses.

| Fetal CMV Infection | No. Cases | Mean Optical Dentsity (range) | | | |
|---|---|---|---|---|---|
| | | Hsp60 | | Hsp70 | |
| | | IgG | IgM | IgG | IgM |
| Positive | 18 | 1.32 (0.64–2.91) | 0.19 (0.08–0.55) | 0.23[a] (0.06–0.41) | 0.17[b] (0.07–0.35) |
| Negative | 35 | 1.26 (0.50–2.97) | 0.17 (0.06–0.33) | 0.23[a] (0.15–0.38) | 0.06 (0.03–0.13) |
| Controls | 28 | 1.29 (0.55–3.07) | 0.16 (0.06–0.26) | 0.07 (0.05–0.08) | 0.06 (0.05–0.08) |

[a] p < 0.0001 vs. control group;
[b] p < 0.0001 vs. CMV-negative and control groups.

Example 4

Relation Between IgM and Anti-hsp70 Optical Density Values and Fetal Pathology

The relation between IgM anti-hsp70 optical density values and fetal pathology is shown in Table 2. Follow-up of the 3 CMV culture- and PCR- negative fetuses who were low-positive for IgM anti-hsp70 revealed no CMV infection at birth. Subsequent screening showed no detectable consequences of CMV infection in two of these infants (18–24 month period). The third infant was lost to follow-up. Fetuses whose sera yielded a low positive optical density value below 0.130 (6 cases), or who were negative for anti-hsp70 IgM (one case) were normal at delivery and without any apparent disease during a median follow-up period of 31 months (range 5–76 months). For fetuses whose sera yielded an optical density of 0.130–0.140 for anti-hsp70 IgM there was one stillbirth and 3 pregnancy terminations. However, immunohistologic examination identified only a single CMV inclusion in the lung of one of the terminated fetuses; the two other terminations and the stillbirth had no evidence of CMV inclusions. Fetuses whose sera yielded an anti-CMV IgM optical density of 0.191 or higher had easily identifiable evidence of CMV-related pathology, CMV-inclusions in all tissues, especially in brain, and neurological sequela.

Bodéus M, Hubintont C, Bernard P, Bouckaert A, Thomas K, Goubau P. Prenatal diagnosis of human Cytomegalovirus by culture and polymerase chain reaction: 98 pregnancies leading to congenital Infection. *Prenat. Diagn.* (1999) 19:314–317.

Daffos F, Capella-Pavlovski M, Forestier F. Fetal blood sampling with use of a needle guided by ultrasound: A study of 606 consecutive cases. *Am. J. Obstet Gynecol.* (1985) 153:655–660.

Demmler G J. In *Viral Disease in Pregnancy,* Gonik B (ed.). Springer-Verlag: New York, Berlin, Heidelberg; 69–91.

Donner C, Liesnard C, Content J, Busine A, Aderca J, Rodesch F. Prenatal diagnosis of 52 pregnancies at risk for congenital cytomegalovirus infection. *Obstet. Gynecol.* (1993) 82:481–486.

Grangeot-Keros L and Cointe D. Diagnosis and prognostic markers of HCMV infection. *J. Clin. Virol.* (2001) 21:213–221.

Grangeot-Keros L, Mayaux M J, Lebon P, Freymuth F, Eugene G, Stricker R, et al. Value of Cytomegalovirus IgG avidity index for the diagnosis of primary CMV infection in pregnant women. *J. Infect. Dis.* (1997) 175:944–946.

Hagay Z L, Biran G, Ornoy A, Reece E A. Congenital cytomegalovirus infection: A long-standing problem still seeking a solution. *Am. J. Obstet Gynecol.* (1996) 174:241–245.

Hagemeier C, Walker S M, Sissons P J, Sinclair J H. The 72K IE1 and 80K IE2 proteins of human cytomegalovirus independently trans-activate the c-fos, c-myc, and hsp70 promotors via basal promoter elements. *J. Gen. Virol.* (1992) 73:2385–2393.

Hogge W A, Buffone G J, Hogge J S. Prenatal diagnosis of cytomegalovirus infection: a preliminary report. *Prenat. Diagn.* (1993) 13:131–136.

Hohlfeld P, Vial Y, Maillard-Brignon C, Vaudauz B, Fawer C L. Cytomegalovirus fetal infection: prenatal diagnosis. *Obstet. Gynecol.* (1991) 78:615–618.

Lazzarotto T, Dalla Casa B, Campisi B, Landini M P. Enzyme-linked immunoadsorbent assay for the detection of cytomegalovirus-IgM: Comparison between eight commercial kits, immunofluorescence, and immunoblotting. *J. Clin. Lab. Anal.* (1992) 6:216–218.

Lazzarotto T, Spezzacatena P, Pradelli P, Abate D A, Varani S, Landini M. Avidity of immunoglobulin G directed against human cytomegalovirus during primary and secondary infections in immunocompetent and immunocompromised subjects. *Clin. Diagn. Lab. Immunol.* (1997) 4:469–473.

Lévy R, Najioullah F, Thouvenot D, Bosshard S,Aymard M, Lina B. Evaluation and comparison of PCR and hybridization methods for rapid detection of cytomegalovirus in clinical samples. *J. Virol. Methods* (1996) 62:103–111.

Marthin T, Liedgren S, Hammer M. Transplacental needle passage and other risk-factors associated with second trimester amniocentesis. *Acta. Obstet. Gynecol. Scand.* (1997) 76:728–732.

Stagno S, Pass R F, Cloud G et al. Primary cytomegalovirus infection in pregnancy. Incidence, transmission to fetus and clinical outcome. *JAMA* (1986) 256:1904–1908.

Towbin et al. Electrophoretic transfer of proteins from polyacrylamide gels to nitrocellulose sheets: procedure and some applications. *PNAS* (1979) 76:4350–4354.

Towbin et al. Immunoblotting and dot immunobinding—current status and outlook. *J. Immunol. Methods* (1984) 72:313–340.

Welch W J. Heat shock proteins functioning as molecdular chaperones: their roles in normal and stressed cells. *Philosophical Transactions of the Royal Society of London B Biological Sciences* (1993) 339:327–333.

Witkin S S, Askienazy-Elbhar M, Henry-Suchet J, Belaisch-Allart J, Tort-Grumbach J, Sarjdine K. Circulating antibodies to a conserved epitope of the *Chlamydia trachomatis* 60 kDa heat shock protein in infertile couples and its relationship to antibodies to *C. trachomatis* surface antigens and the *Escherichia coli* and human HSP60. *Human Reprod.* (1998) 13:1175–1179.

What is claimed is:

1. A method for detecting the presence of cytomegalovirus in a fetal sample, the method comprising:
   i) obtaining a fetal sample from an expectant mother infected with cytomegalovirus, wherein the fetal sample is a fluid in the fetus or enclosed by the amniotic sac; and
   ii) determining the amount of anti-heat shock protein 70 IgM antibodies or the quantity of detectable signal that is a measure of the amount of anti-heat shock protein 70 IgM antibodies in the fetal sample,
   wherein an elevated amount of anti-heat shock protein 70 IgM antibodies or quantity of detectable signal indicates the presence of cytomegalovirus in the fetal sample.

2. A method according to claim 1, wherein the fetal sample is cord blood.

3. A method according to claim 1, wherein the fetal sample is fetal sera.

4. A method according to claim 1, wherein the fetal sample is amniotic fluid.

5. A method according to claim 1, wherein the mother has a primary cytomegalovirus infection.

6. A method according to claim 1, wherein the mother has a recurrent cytomegalovirus infection.

7. A method according to claim 1, wherein the anti-heat shock protein 70 antibody is an antibody to a heat shock protein 70 complexed to a cytomegalovirus viral protein.

8. A method according to claim 1, wherein the amount of anti-heat shock protein 70 antibodies or quantity of detectable signal in the fetal sample is an amount or quantity sufficient to cause congenital cytomegalovirus syndrome.

9. A method according to claim 1, wherein the amount of anti-heat shock protein 70 antibodies or quantity of detectable signal in the fetal sample is an amount or quantity which is asymptomatic at birth.

10. A method for monitoring cytomegalovirus infection in a human fetus, the method comprising:
    i) obtaining a first fetal sample from an expectant mother infected with cytomegalovirus, wherein the fetal sample is a fluid in the fetus or enclosed by the amniotic sac;
    ii) determining the amount of anti-heat shock protein 70 IgM antibodies present in the first fetal sample,
    iii) obtaining a subsequent fetal sample, and
    iv) determining the amount of anti-heat shock protein 70 IgM antibodies in the subsequent fetal sample,
    wherein a change in the amount of anti-heat shock protein 70 IgM antibodies in the first sample compared to the subsequent sample indicates a change in the infection, thereby monitoring the cytomegalovirus infection in the fetus.

11. A method according to claim 10, wherein the fetal sample is cord blood.

12. A method according to claim 10, wherein the fetal sample is fetal sera.

13. A method according to claim 10, wherein the fetal sample is amniotic fluid.

14. A method according to claim 10, wherein the presence of anti-heat shock protein 70 antibodies is in the fetal sample in an amount sufficient to cause congenital cytomegalovirus syndrome.

15. A method according to claim 10, wherein the presence of anti-heat shock protein 70 antibodies is in the fetal sample in an amount which is asymptomatic at birth.

16. A method according to claim 10, wherein the mother has a primary cytomegalovirus infection.

17. A method according to claim 10, wherein the mother has a recurrent cytomegalovirus infection.

18. A method according to claim 10, wherein the anti-heat shock protein 70 antibody is an antibody to a heat shock protein 70 complexed to a CMV viral protein.

19. A method for detecting the presence of cytomegalovirus in a cord blood sample of a neonate, the method comprising:
    i) obtaining the cord blood sample and
    ii) determinin the amount of anti-heat shock protein 70 IgM antibodies or quantity of detectable signal that is a measure of the amount of anti-heat shock protein 70 IgM antibodies in the sample;
    wherein an elevated amount of anti-heat shock protein 70 IgM antibodies or quantity of detectable signal in the sample indicates the presence of cytomegalovirus in the cord blood sample.

20. A method according to claim 19, wherein the anti-heat shock protein 70 antibody is an antibody to a heat shock protein 70 complexed to a CMV viral protein.

21. A method according to claim 19, wherein the amount of anti-heat shock protein 70 antibodies or quantity of detectable signal in the sample is an amount or quantity sufficient to cause late sequelae.

22. A method according to claim 1, wherein the amount of anti-heat shock protein 70 IgM antibodies or the quantity of detectable signal that is a measure of the amount of anti-heat shock protein 70 IgM antibodies in the fetal sample is relative to a control sample.

23. A method according to claim 19, wherein the amount of anti-heat shock protein 70 IgM antibodies or the quantity of detectable signal that is a measure of the amount of anti-heat shock protein 70 IgM antibodies in the sample is relative to a control sample.

* * * * *